United States Patent
Nielsen et al.

(10) Patent No.: US 7,118,891 B2
(45) Date of Patent: Oct. 10, 2006

(54) CRYSTAL HARVEST FROM FERMENTATION BROTH

(75) Inventors: Benny Nielsen, Gislinge (DK); Anders Rancke-Madsen, Charlottenlund (DK); Martin Troen Jorgensen, Roskilde (DK)

(73) Assignee: Novozymes A/S, Bagsvaerd (DK)

( * ) Notice: Subject to any disclaimer, the term of this patent is extended or adjusted under 35 U.S.C. 154(b) by 315 days.

(21) Appl. No.: 10/309,439

(22) Filed: Dec. 4, 2002

(65) Prior Publication Data

US 2003/0129707 A1    Jul. 10, 2003

Related U.S. Application Data

(60) Provisional application No. 60/339,509, filed on Dec. 11, 2001.

(30) Foreign Application Priority Data

Dec. 11, 2001   (DK)  ............................... 2001 01847

(51) Int. Cl.
*C12P 21/06*    (2006.01)

(52) U.S. Cl. ...................................... 435/71.1; 435/272

(58) Field of Classification Search ............... 435/71.1, 435/272
See application file for complete search history.

(56) References Cited

U.S. PATENT DOCUMENTS

| 4,659,667 A | 4/1987 | Brewer et al. |
| 5,445,949 A * | 8/1995 | Koster et al. .............. 435/71.1 |

FOREIGN PATENT DOCUMENTS

| EP | 0 574 050 | 12/1993 |
| FR | 2 679 235 | 1/1993 |
| WO | WO 95/01989 | 1/1995 |
| WO | WO 96/38469 | 12/1996 |

OTHER PUBLICATIONS

Bajpal et al., Biotechnecology Techniques, vol. 4, No. 4., pp. 227-232 (1990).

* cited by examiner

*Primary Examiner*—Herbert J. Lilling
(74) *Attorney, Agent, or Firm*—Jason Garbell

(57) ABSTRACT

A method for producing a crystalline and/or amorphous metabolite suspension from a fermentation broth comprising treating the fermentation broth with one or more coagulants and/or one or more flocculants; and separating the biomass of the fermentation broth from the coagulated and/or flocculated fermentation broth by use of a separation equipment, whereby a crystalline and/or amorphous metabolite suspension is obtained.

8 Claims, No Drawings

CRYSTAL HARVEST FROM FERMENTATION BROTH

CROSS REFERENCE TO RELATED APPLICATIONS

This application claims, under 35 U.S.C. 119, priority of Danish application no. PA 2001 01847, filed Dec. 11, 2001, and the benefit of U.S. application No. 60/339,509, filed Dec. 11, 2001, the contents of which are fully incorporated herein by reference.

TECHNICAL FIELD

The present invention relates to a simple and effective method for obtaining a crystalline and/or amorphous metabolite suspension from a fermentation broth.

SUMMARY OF THE INVENTION

It has surprisingly been found that a simple and effective method for producing a crystalline and/or amorphous metabolite suspension from a fermentation broth may be produced by
(a) treating the fermentation broth with one or more coagulants and/or one or more flocculants; and
(b) separating the biomass of the fermentation broth from the coagulated and/or flocculated fermentation broth by use of a separation equipment, whereby a crystalline and/or amorphous metabolite suspension is obtained.

DETAILED DISCLOSURE OF THE INVENTION

The present invention provides a simple and effective method for producing a crystalline and/or amorphous metabolite suspension from a fermentation broth.

The method of the invention may be applied to an untreated fermentation broth or to a fermentation broth that has first been subjected to, e.g., a pH adjustment, a temperature adjustment, and/or a water dilution.

Metabolites of Interest

The metabolite of interest according to the invention may be an antibiotic such as penicillin or cephalosporin, or a commodity chemical such as citric acid. The metabolite may also be a protein, e.g. a therapeutic protein such as insulin or an enzyme. The enzyme may be a hydrolase, a transferase, a lyase, an isomerase, or a ligase.

In a preferred embodiment, the method is applied to proteases, lipases, amylases, cellulases, and oxidoreductases.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 91/00345, WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 195, 206, 218, 222, 224, 235 and 274.

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544.

Oxidoreductases: Oxidoreductases that may be treated according to the invention include peroxidases (EC 1.11.1.7), and oxidases such as laccases, and catalases (EC 1.11.1.6).

Peroxidases: Preferably, the peroxidase employed in the method of the invention is producible by microorganisms such as fungi or bacteria.

Particularly, a *Coprinus* peroxidase is preferred, in particular a *C. macrorhizus* or *C. cinereus* peroxidase, or a variant thereof.

Laccases and Laccase Related Enzymes: In the context of this invention, laccases and laccase related enzymes contemplate any laccase enzyme comprised by the enzyme classification (EC 1.10.3.2), any chatechol oxidase enzyme comprised by the enzyme classification (EC 1.10.3.1), any bilirubin oxidase enzyme comprised by the enzyme classification (EC 1.3.3.5) or any monophenol monooxygenase enzyme comprised by the enzyme classification (EC 1.14.18.1).

The microbial laccase enzyme may be derived from bacteria or fungi (including filamentous fungi and yeasts) and suitable examples include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinus*, e.g. *C. plicatilis* and *C. cinereus, Psatyrella, Myceliophthora*, e.g. *M. thermophila, Schytalidium, Polyporus*, e.g., *P. pinsitus, Phlebia*, e.g., *P. radita* (WO 92/01046), or *Coriolus*, e.g., *C. hirsutus*(JP 2-238885).

Fermentations

The fermentation broth according to the invention may be obtained from any microorganism of any genus known in the art.

In a preferred embodiment, the metabolite of interest may be obtained from a bacterial or a fungal source. For example, the metabolite of interest may be obtained from a gram positive bacterium such as a *Bacillus* strain, e.g., *Bacillus alkalophilus, Bacillus amyloliquefaciens, Bacillus brevis, Bacillus circulans, Bacillus coagulans, Bacillus lautus, Bacillus lentus, Bacillus clausii, Bacillus licheniformis, Bacillus megaterium, Bacillus stearothermophilus, Bacillus subtilis*, or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

The metabolite of interest may be obtained from a fungal source, e.g. from a yeast strain such as a *Candida, Kluyveromyces, Pichia, Saccharomyces, Schizosaccharomyces*, or *Yarrowia* strain, e.g., *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain.

In a preferred embodiment the metabolite of interest may be obtained from a filamentous fungal strain such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* strain, in particular the metabolite of interest may be obtained from an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* strain.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

For purposes of the present invention, the term "obtained from" as used herein in connection with a given source shall mean that the metabolite of interest is produced by the source or by a cell in which a gene from the source has been inserted.

The microbial strain may be fermented by any method known in the art. The fermentation medium may be a complex medium comprising complex nitrogen and/or carbon sources, such as soybean meal, cotton seed meal, corn steep liquor, yeast extract, casein hydrolysate, molasses, and the like. The fermentation medium may be a chemically defined media, e.g. as defined in WO 98/37179.

The fermentation may be performed as a fed-batch, a repeated fed-batch or a continuous fermentation process.

Coagulants and Flocculants

According to the invention a useful coagulant may be a salt such as one selected from the group consisting of the group I metal salts, the group II metal salts, and the group III metal salts, or mixtures thereof; in particular Ca-, Mg- and Al-salts. Preferred salts are ammonium, phosphate, sulfate, carbonate, and citrate salts. Halogenide salts, formiates and acetates may also be applicable, especially chloride salts such as calcium chloride.

Useful salt concentrations will be in the range of 0.1–40% (w/w); preferably in the range of 0.2–20% (w/w); more preferably in the range of 0.3–6% (w/w).

According to the invention another useful coagulant is a short chained polymer, in particular a cationic polymer with a molecular weight in the range of from 20 Daltons to 500000 Daltons, such as a tertiary or a quaternary polyamine, e.g. C521 obtainable from Cytec Industries, Poly-DADMAC's (Di-allyl Dimethyl Ammonium Chlorid), e.g. C591, or Aluminimu sources such as polyaluminumchlorohydrate: Al2(OH)5Cl, e.g. GC850 obtainable from Gulbrandsen.

Useful short chained polymer concentrations will typically be in the range of 0.1–25% (w/w); preferably in the range of 0.2–20% (w/w); more preferably in the range of 0.3–15% (w/w).

It will often be an advantage to add more than one coagulant, e.g. a salt and one or more short chained polymers.

According to the invention a useful flocculant may be an inorganic and/or organic polymer which may be cationic, anionic or non-ionic.

A useful cationic polymer is a polyamine, and a useful anionic polymer is a polyacrylamid.

Useful polymer concentrations will be in the range of 0.01–1.0% (w/w); preferably in the range of 0.05–0.5% (w/w).

Separation Equipment

According to the invention a useful separation equipment is any design of a two-phase centrifuge, especially a continuous sludge decharging centrifuge, a decanter or a cyclone.

It may in some cases be an advantage to add a flocculatant, in particular an anionic polymer, to the separation equipment in order to avoid biomass in the crystalline and/or amorphous suspension (see Example 1).

Crystalline and/or Amorphous Suspension

It is possible to coagulate and/or flocculate the metabolite fermentation broth so that the crystalline and/or amorphous metabolites are in the right separation zone and thus can be separated in e.g. a centrifuge process into a biomass fraction (with a very low metabolite concentration), the crystalline and/or amorphous metabolite fraction (with a high metabolite concentration) and the supernatant fraction (with a very low metabolite concentration). The coagulation and/or the flocculation has the effect that the crystalline and/or amorphous metabolites are not incorporated in the flocks, so after the biomass has been separated the crystalline and/or amorphous metabolites may be further concentrated in order to achieve the wanted yield.

The suspension achieved according to the invention may be further purified in a variety of ways such as by using grinding, sieving, drying, filtration, centrifugation, re-crystallisation, chromatographic methods, adsorption processes and/or two-phase extraction.

The invention is further illustrated in the following examples which are not intended to be in any way limiting to the scope of the invention as claimed.

EXAMPLE 1

Harvest of Protease Crystals from Fermentation Broth

A fermentation broth containing a mutated subtilisin protease obtained from a *Bacillus* sp. disclosed in WO 91/00345 was subjected to the method of the invention.

The protease fermentation broth was run in production scale based on the following coagulation/flocculation recipe:

| | |
|---|---|
| Temperature: | 12° C. |
| Dilution: | 2 times with water |
| CaCl$_2$ (36% w/w): | 4.7% |
| C521 (17% w/w): | 12.0% |
| GC-850 (20% w/w): | 5.0% |
| NaOH (3% w/w): | pH 7.5 |

The trial was made on an entire protease batch using one Westfalia SB60 centrifuge.

The feed contained 17–20% wet sludge volume.

The centrifuge used was equipped with a nozzle bowl and a standardized sludge flow of 4 m3/hr.

The trial ran 21 hours where the feed flow was step-wise increased from 7.5 m3/h to 9.5 m3/hr. In order to avoid biomass in the centrate, an anionic polymer was added at feed flows above 7.5 m3/hr.

The anionic polymer solution used was 0.15% (w/w) (polyacrylamid).

The percent wet crystal volume was measured in the centrate during the trial and used as yield indicator.

Table 1 shows the results.

Instead of using a Westfalia SB60 centrifuge a test was run using two Alfa Laval NX418 decanters as a first step extraction.

The test shows that the centrifuge process is superior to the decanter process in terms of capacity and yield.

TABLE 1

| | Decanter | Centrifuge | Interval between Empting the bowl |
|---|---|---|---|
| Flow | 2000 l/h | 7500 l/h | 15 min. |
| Anionic polymer | 400 l/h | 0.0 l/h | |
| % crystal | 0.4–0.6% | 0.6–1.0% | |
| Flow | | 8000 l/h | 15 min. |
| Anionic polymer | | 50 l/h | |
| % crystal | | 0.6–1.2% | |
| Flow | | 8500 l/h | 15 min. |
| Anionic polymer | | 100 l/h | |
| % crystal | | 0.6–1.5% | |
| Flow | | 9000 l/h | 15 min. |
| Anionic polymer | | 200 l/h | |
| % crystal | | 0.7–1.5% | |
| Flow | | 9500 l/h | 20 min. |
| Anionic polymer | | 250 l/h | |

TABLE 1-continued

| | Decanter | Centrifuge | Interval between Empting the bowl |
|---|---|---|---|
| % crystal | | 0.7–1.5% | |
| % sludge | | 0.1–0.3% | |

EXAMPLE 2

Harvest of Alpha-Amylase Crystals from Fermentation Broth

An alpha-amylase obtained from a *Bacillus* sp. strain disclosed in SEQ ID NO: 2 of WO 95/26397 with a double deletion (D183*+G184*) as described in WO 96/23873, was fermented. The alpha-amylase fermentation broth was taken out from production harvest tank and tests were done in lab based on the following flocculation recipe:

| | |
|---|---|
| Temperature: | 12° C. |
| Dilution: | 2 times with water |
| CaCl$_2$ (36% w/w): | 4.7% |
| C521 (17% w/w): | 12.0% |
| GC-850 (20% w/w): | 5.0% |
| NaOH (3% w/w): | pH 7.5 |

It was possible to flocculate the alpha-amylase fermentation broth, so that the enzyme crystals were in the right separation zone (limits particles) and thus be separated in a centrifuge process.

The activity in the supernatant of the flocculated broth showed that only 0.8% of the alpha-amylase enzyme was in the solution.

The invention claimed is:

1. A method for producing a crystalline and/or amorphous metabolite suspension from a fermentation broth comprising
   (a) treating the fermentation broth with one or more salts and one or more polymers; and
   (b) separating the fermentation broth, by use of a separation equipment, into a biomass fraction, a crystalline and/or amorphous metabolite fraction, and a supernatant fraction, wherein the separation equipment is selected from the group consisting of a continuous sludge decharging centrifuge.

2. The method according to claim 1, wherein the metabolite is a protein.

3. The method according to claim 1, wherein the protein is an enzyme.

4. The method according to claim 3, wherein the enzyme is a protease, a lipase, a cellulase, an amylase or an oxidoreductase.

5. The method according to claim 1, wherein the salt is selected from the group consisting of Ca-, Mg- and Al-salts.

6. The method according to claim 1, wherein the polymer has a molecular weight in the range of from 20 Daltons to 500000 Daltons.

7. The method according to claim 1, wherein the polymer is a cationic or an anionic polymer.

8. The method according to claim 7, wherein the polymer is a polymine or a polyacrylamid.

* * * * *